US005890610A

United States Patent [19]

Jansen et al.

[11] Patent Number: 5,890,610

[45] Date of Patent: Apr. 6, 1999

[54] VIAL CONNECTOR ASSEMBLY FOR A MEDICAMENT CONTAINER

[76] Inventors: Hubert Jansen, Le Domain de L'Enclos Bât. E, 38560 Haute Jarrie; Jean Claude Thibault, 18 Rue de Cuvilleux, 38120 Saint Egreve, both of France; Bernard Sams, 22 Avondale Avenue, London N12 8 EJ, England

[21] Appl. No.: 962,897

[22] Filed: Nov. 3, 1997

Related U.S. Application Data

[63] Continuation of Ser. No. 714,907, Sep. 17, 1996, abandoned.

[51] Int. Cl.[6] .......... B65D 39/00; A61B 19/00

[52] U.S. Cl. .......... 215/253; 215/274; 215/276; 215/DIG. 3; 604/403; 604/412; 604/414

[58] Field of Search .......... 215/249, 251, 215/253, 274, 276, DIG. 3; 604/403, 412, 414

[56] References Cited

U.S. PATENT DOCUMENTS

| | | | |
|---|---|---|---|
| 3,587,897 | 6/1971 | Rohde | 215/249 |
| 4,624,393 | 11/1986 | Lopez . | |
| 5,085,332 | 2/1992 | Getting et al. | 215/249 |
| 5,269,429 | 12/1993 | Schumacher | 215/249 |
| 5,314,084 | 5/1994 | Folta et al. | 215/249 |
| 5,316,163 | 5/1994 | Von Schuckmann | 215/249 |
| 5,348,174 | 9/1994 | Velicka | 215/277 |
| 5,358,501 | 10/1994 | Meyer . | |
| 5,421,469 | 6/1995 | Lee | 215/274 |
| 5,562,219 | 10/1996 | De Pous et al. | 215/274 |

FOREIGN PATENT DOCUMENTS

| | | |
|---|---|---|
| 0 161 797 | 11/1985 | European Pat. Off. . |
| WO 97/10156 | 3/1997 | WIPO . |

*Primary Examiner*—Stephen K. Cronin

[57] ABSTRACT

A connector assembly provided for efficient flow of liquid into and/or out of a vial, such as a vial containing a lyophilized drug. The connector assembly features a collar mountable to the rim of the vial in a locked position and thereafter removable by an end-user when disposal of the device is desired. A protective cap mountable over the collar includes an annulus-type ring at its proximal end which mounts over locking structure associated with the collar. The ring is secured to the protective cap via one or more user-severable connections. As the cap is urged proximally, the ring places the collar in the locked position with the vial rim, exerting an inwardly-directed force onto the locking structure to secure the collar to the vial rim. The cap can be separated from the ring at its user-severable connections, and the device used in its ordinary matter. When disposal is desired, the ring may be urged proximally out of engagement with the locking structure of the collar. The collar may thereafter be removed from the vial to facilitate separate disposal of those components.

15 Claims, 13 Drawing Sheets

VIAL CONNECTOR ASSEMBLY FOR A MEDICAMENT CONTAINER

This application is s continuation of application Ser. No. 8/714,907, filed Sept. 17, 1996 now abandoned.

BACKGROUND OF THE INVENTION

1. Field of the Invention.

The subject invention relates to a connector assembly for a vial, and more particularly, to a connector assembly for a vial which can be safely removed from the vial after use to facilitate the disposal of the various components.

2. Description of the Prior Art.

Many drugs are presented in dry form to achieve a longer shelf life. These drugs are reconstituted by a suitable solvent into liquid form for delivery to a patient. One type of dry drug is a lyophilized drug.

In the art, there are a number of ways to store dry drugs such as lyophilized drugs in a form conducive to reconstitution and delivery. Some of these products are exemplified, for example, by the MONOVIAL ®-brand prefillable drug delivery devices manufactured and sold by Becton Dickinson Pharmaceutical Systems of Le Pont de Claix, France. Such systems are further exemplified, for instance, in U.S. Pat. No. 5,358,501, issued to Gabriel Meyer on Oct. 25, 1994. While there are variations of such systems, in general, they feature vials made of glass or suitable plastic materials, in which a selected dose of a lyophilized drug may be stored. The vial is generally sealed to prevent deterioration or contamination of the drug. The dry drug may be reconstituted with a liquid solvent shortly prior to use, and the now reconstituted drug solution may be administered to a patient.

Various components are employed with the prefillable drug-delivery systems described above. For instance, the vials are typically provided with a vial connector assembly to enable attachment of the vial to a source of solvent to reconstitute the dry drug. The same vial connector is also normally used to attach the vial to an intravenous fitting to deliver the reconstituted drug to a patient. Vial connectors such as used with the prefillable drug delivery systems described above typically include one or more components necessary for the function of the system. For instance, one or more rubber stopper or membrane components are provided to seal the vial until such time as access to the drug, in its dry or liquid form, is desired. A fluid transfer device, such as a needle or spike, is also provided, both to provide means for introducing solvent into the vial and for delivering the reconstituted drug out of the vial. Generally, a collar component is provided adjacent the rim of the vial to secure the various parts, such as the fluid transfer device and the sealing components, associated with the vial connector.

Depending on the configuration of the prefillable drug-delivery system, the system might be activated by moving the collar relative to the vial rim, wherein the fluid transfer device and sealing components are fixed relative to the collar, or by moving the fluid transfer device and sealing components relative to the vial, wherein the collar is fixed relative to the vial rim movable manner relative to the collar. Accordingly, depending on the configuration, the system can be activated either by causing motion between the collar and the rim, or by causing motion between the fluid transfer device and/or sealing components relative to the collar.

One aspect of the aforementioned systems is that subsequent to use, the various components, such as the fluid transfer device, sealing components, and the collar itself remain fixed to the vial. Here, once the drug has been delivered to the patient, the entire system is disposed of whole in a sterile manner. Owing to the different materials used for the various components, benefits may be realized in configuring a system wherein the components can be separated from one another in a safe manner to facilitate disposal. For instance, certain governmental regulations or accepted practices may encourage disposing of the vial, which contained the drug in its dry and reconstituted forms, separately from the transfer assembly.

SUMMARY OF THE INVENTION

The subject invention is directed to a connector assembly for use with a vial. The vial includes a bottom wall and an upstanding side wall. A shoulder extends inwardly from the top end of the side wall and a tubular neck extends upwardly from the shoulder to an open top. An annular rim may extend around portions of the neck that define the open top. Portions of the vial between the tubular neck and the bottom wall define an enclosure in which a lyophilized drug or a drug solution may be stored.

A novel aspect of the connector assembly in accordance with the present invention is that it is mountable to the neck of the vial in a manner such that it may be safely removed by a practitioner, such that the connector assembly may be disposed of separately from the vial. The connector assembly can be employed with various fluid transfer devices, such as a needle, a spike or a luer, as means for introducing solvent into the vial and for delivering a reconstituted drug out of the vial. Various stoppers and membrane components may be provided in conjunction with the connector assembly to seal the vial until such time as access to the drug, in its dry or liquid form, is desired.

The connector assembly includes a collar mountable to the rim of the vial neck. The collar includes a proximal end, a distal end, and a sidewall therebetween. A plurality of deflectable latches are provided adjacent the proximal end of the collar. The plurality of deflectable latches each include locking means deflectable about a side portion of the rim for secure engagement with the underside of the rim In one configuration, the locking means can be formed as a proximally facing, inwardly canted locking surface provided adjacent the proximal end of each of the deflectable latches.

The connector assembly includes a protective cap mountable about the sidewall portion of the collar which cooperates with the collar to secure the connector assembly to the vial rim. The protective cap features an open proximal end, a closed distal end, and a shield wall formed therebetween. A ring is provided adjacent the open proximal end of the protective cap. The ring features an annulus-section with an interior surface cooperable with structure associated with the deflectable latches and is connected to the proximal end of the protective cap by one or more user-severable connections. In one embodiment, the user-severable connections are formed as one or more frangible sections formed between the proximal end of the cap and a distal end end of the ring. The ring may include a rib element formed at a proximal end thereof The rib element may cooperate with structure provided on the deflectable latches to prevent further distal movement of the ring after the collar is urged into a locked position with the vial rim. The interior surface of the annular section may define a diameter equal to, or slightly less than, a diameter defined by a diametrically opposed pair of deflectable latches, such that the annulus section will apply an inwardly-directed holding force onto the deflectable latches. The inwardly directed force will retain the collar in a locked position respective of the vial rim.

The device may be supplied to a pharmaceutical manufacturer in a manner to enable processing and filling of the vial with a desired drug. After the drug is filled into the vial, the collar can be lockingly secured to the vial rim for shipment to an end user. The collar, together with the fluid transfer device and the various sealing stoppers and/or membranes associated with the connector assembly, are positioned in a manner to seal the open top of the vial. The protective cap is then mounted about the sidewall portion of the collar. If provided, sterility ribs provided on an interior portion of the cap cooperate with the sidewall of the collar to provide added sealing security for the drug retained within the vial as well as for the various components associated with the connector assembly.

Continued proximal motion of the cap relative to the collar will cause the annulus section to engage the deflectable latches, such that cap and collar are both moved proximally relative to the rim. The action of the protective cap against the collar and, in particular, engagement forces exerted between the annulus section of the ring and the deflectable latches of the collar, causes the deflectable latches, and particularly the locking means associated therewith, to move into secure engagement with an underside portion of the rim. The annulus section proceeds proximally relative to the collar, such that the interior surface of the annulus-section is disposed in covering relationship with the deflectable latches of the collar. The rib element provided at the proximal end of the ring retains the ring in fixed position relative to the deflectable latches in a manner such that the ring cannot be further removed in a distal direction. Accordingly, inwardly directed forces are exerted by the annulus-section onto the deflectable latches, to hold the collar in locked position relative to the rim. The device may thus be shipped to an end-user.

The device may be activated by an end-user by first removing the protective cap from the ring by disrupting the user-severable connections. The fluid transfer device and/or sealing stoppers or membranes provided with the connector assembly can be activated in accordance with their function, and the dry drug held in the vial reconstituted and delivered. After the drug has been delivered, the ring may be displaced proximally relative to the collar to free the deflectable latches from engagement with the interior surface of the annulus section. A force may thereafter be applied to the collar to cause the latches to deflect distally about the side section of the rim to remove the collar from the vial. The vial and connector assembly may thus be disposed of separately in accordance with applicable governmental regulations or industry practices.

DETAILED DESCRIPTION OF THE PREFERRED EMBODIMENTS

Figure 1:
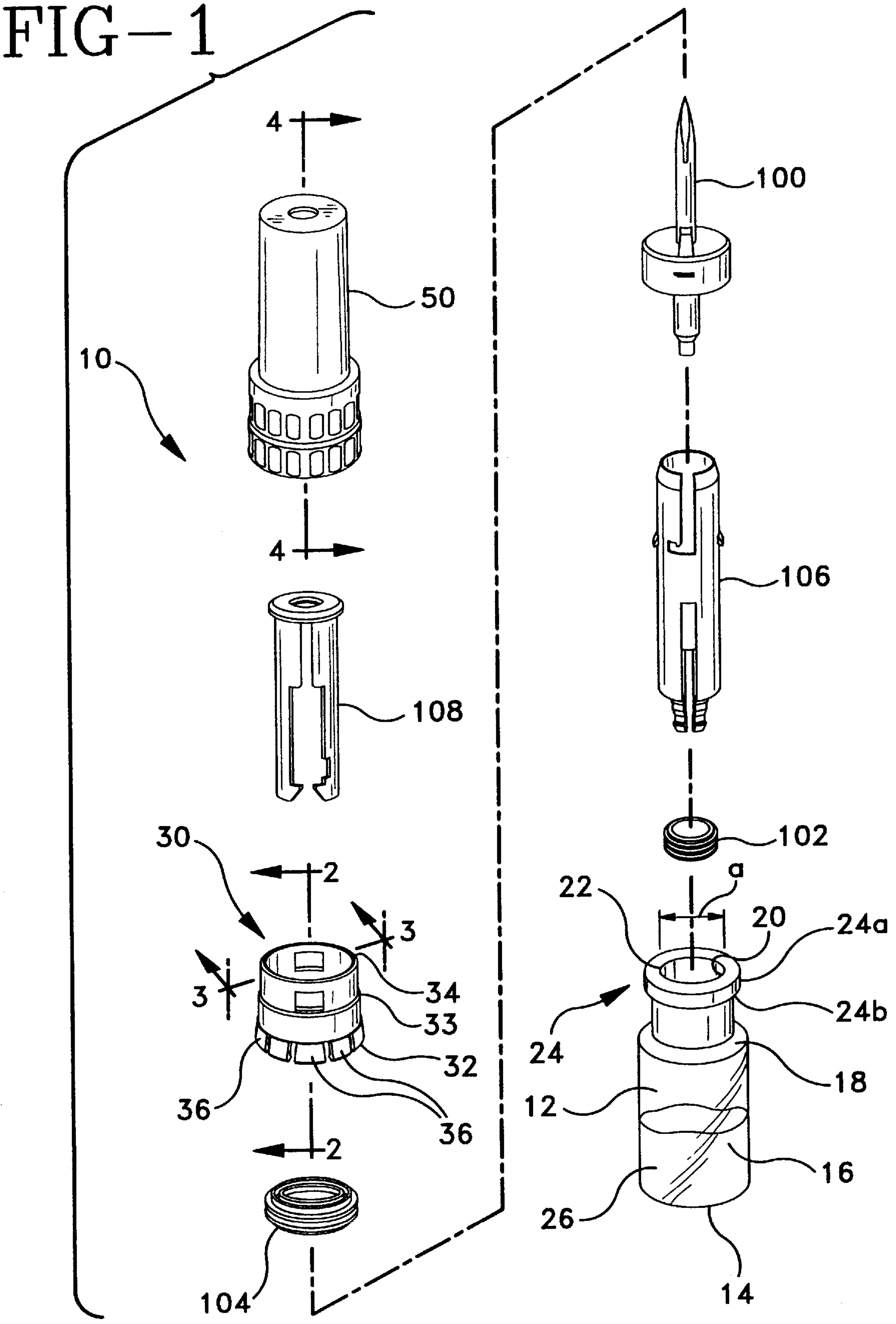
FIG. 1 is an exploded view of one embodiment of a vial connector assembly in accordance with the present invention.

A connector assembly in accordance with the subject invention is identified generally by the numeral 10 in FIG. 1. The connector assembly 10 is used with a vial 12 having a bottom wall 14, a cylindrical side wall 16 extending upwardly from bottom wall 14, a shoulder 18 extending inwardly and upwardly from the end of cylindrical side wall 16 remote from bottom wall 14, and a cylindrical neck 20 of inside diameter “a” extending upwardly from shoulder 18. Neck 20 terminates at an open top 22. Top 22 is characterized by an annular rim 24 projecting outwardly thereabout. Annular rim 24 is characterized by a side portion **24*a* and an underside portion 24*b***.

Vial 12 is provided with a lyophilized drug 26 stored therein. Connector assembly 10 functions to safely seal lyophilized drug 26 in vial 12 and to permit a solvent to be added to vial 12 for mixing with lyophilized drug 26 and forming a drug solution. Connector assembly 10 further enables delivery of the drug solution to an IV set for administration to a patient.

For purposes of illustration but not of limitation, connector assembly 10 in accordance with the subject invention is illustrated with various ancillary components not limiting the scope of applicability of the invention described and claimed herein. For example, connector assembly 10 as described herein is shown with a fluid transfer device 100 configured as a conventional spike. It will be evident to the skilled artisan that other fluid transfer devices, such as luer fittings, pointed needle cannulae, or the like may be employed with the connector assembly 10 of the present invention described herein. Fluid transfer device 100 may include structure 106 serving to retain various vial sealing components. Here, there is illustrated a stopper 102 which serves to seal vial neck 20. Also illustrated is a secondary seal 104 that may be disposed about fluid transfer device 100. It will be explicitly understood by the skilled artisan that other vial sealing devices may be used. Furthermore, there is shown a retractable shield 108 enabling the fluid access device to be shielded so as to prevent inadvertent touch contact with fluid transfer device 100. It will be explicitly understood by the skilled artisan that other shielding devices may be employed with the connector assembly 10 as herein described. For instance, the shielding devices described in U.S. Pat. No. 5,358,501 may be used with equal effect with the connector assembly described and claimed herein.

Figure 2:
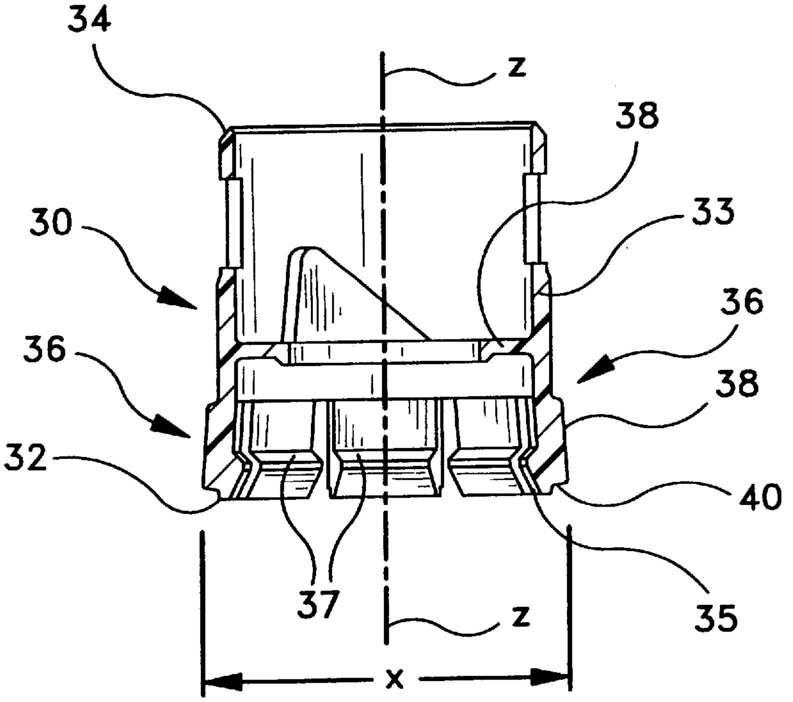
FIG. 2 is a cross-sectional view of the collar taken along line 2—2 of FIG. 1.

Turning now to explanation of connector assembly 10, there is provided a generally annular collar 30. As shown most clearly in FIGS. 1–3, collar 30 has opposed proximal and distal ends 32 and 34, respectively. Proximal end 32 of collar 30 is defined by a plurality of deflectable latches 36 dimensioned to retain collar 30 in a locked position respective of annular rim 24, as well as to permit an end user to safely remove collar 30 from the rim when it is desired to dispose of the connector assembly separately from the vial. Portions of collar 30 between proximal and distal ends 32 and 34 define a sidewall 33. Within sidewall 33 there may be provided radially inwardly extending annular ledge 38 having an inside diameter approximately equal to the inside diameter "a" of neck 20 of the vial 12. Ledge 38 may be provided for mounting fluid transfer components utilizable with the connector assembly of the present invention.

Figure 3:
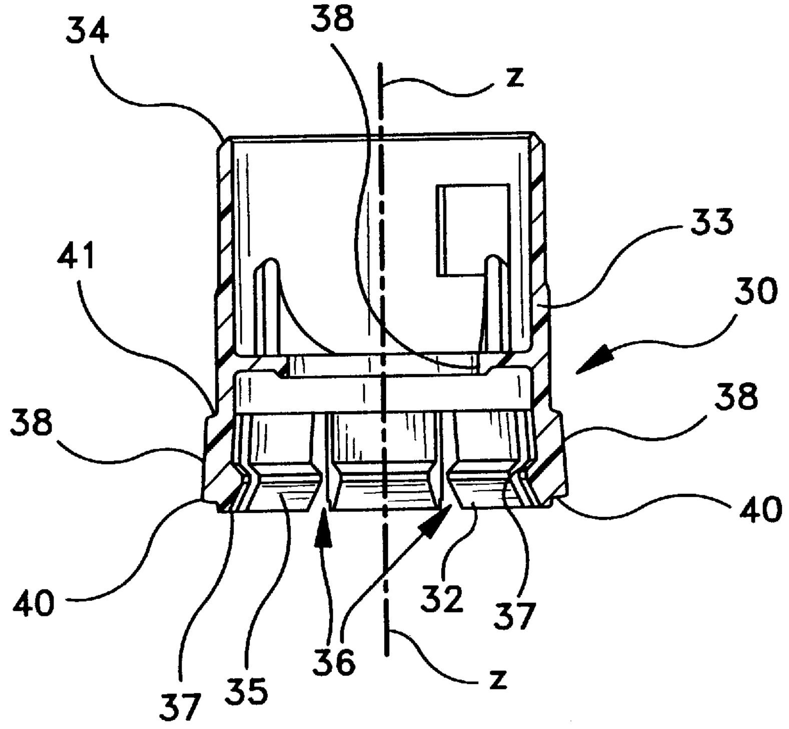
FIG. 3 is another cross-sectional view of the collar, taken along line 3—3 of FIG. 1.
Figure 4:
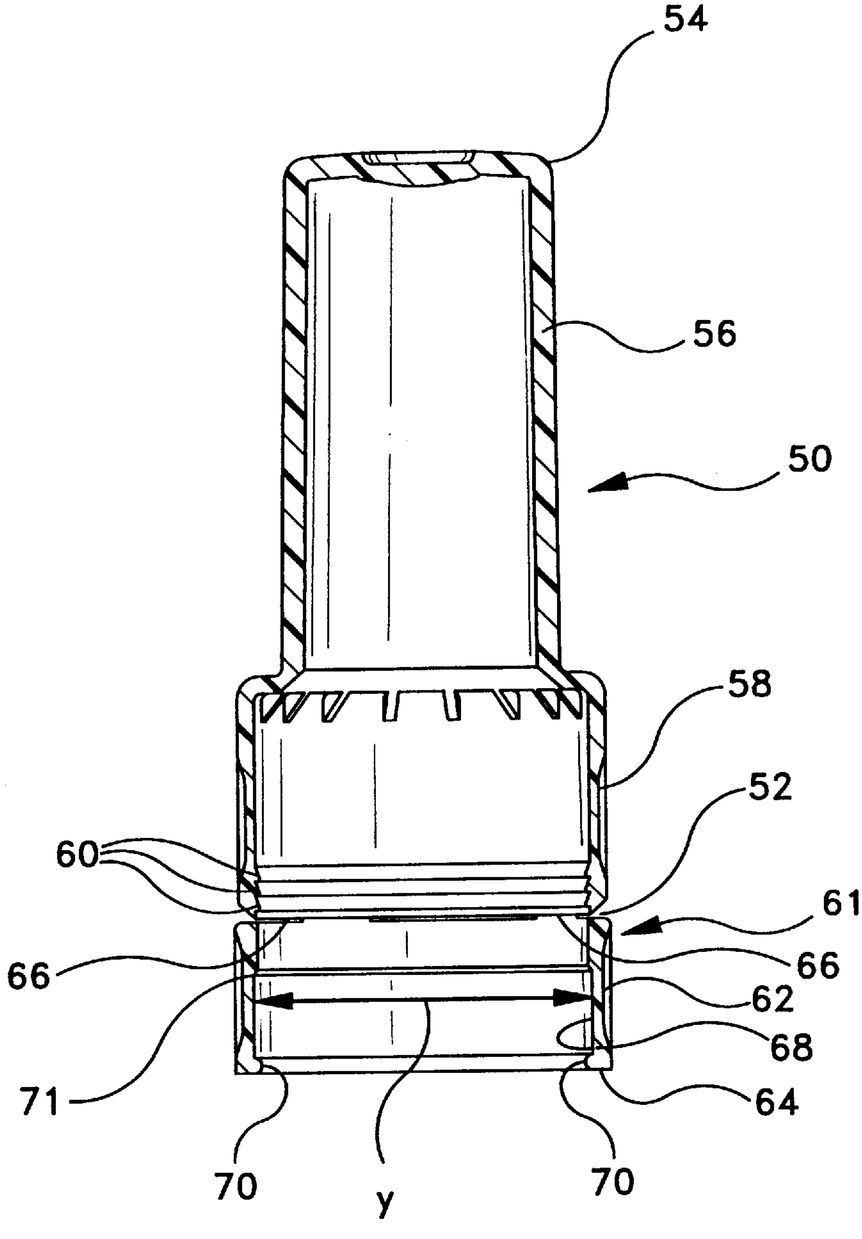
FIG. 4 is a cross-sectional view of the cap, taken along line 4—4 in FIG. 1.

Deflectable latches 36 each include a proximally facing, outwardly-canted surface 35 and a distally facing, inwardly canted locking surface 37. Outwardly-canted surface 35 facilitates proximal movement of collar 30 over rim 24 for movement of the connector assembly into locked position with the rim. Locking surface 37 is configured on each of deflectable latches 36 for securely engaging underside portion 24b of the rim when collar 30 is locked to the rim. Deflectable latches 36 each feature an engagement surface 38 disposed on an exterior portion of the latches. Engagement surface 38 can be formed as an outside portion of latches 36 in a manner so as to be raised from the plane defined by sidewall 33 of the collar. As seen in FIG. 3, a diametrically opposed pair of engagement surfaces 38 define a diameter "X". As illustrated, latches 36 are preferably formed such that they can slightly outwardly from a central axis "Z" running through collar 30 before the collar is locked to the rim. A proximal end of engagement surface 38 terminates before proximal end 32 of the collar to define a notch 40.

A removable safety cap 50 is provided for use with connector assembly 10. Removable safety cap 50 includes an open proximal end 52, a closed distal end 54, and a shield wall 56 formed therebetween. Cap 50 is configured to fit over the various components, such as the fluid transfer device or safety shield, provided for use with the connector assembly 10. Cap 50 may feature enlarged skirt portion 58 adjacent proximal end 52. Skirt portion 58 may feature one or more sealing ribs 60 which come into contact with sidewall 33 of collar 30 when cap 50 is placed thereover to enhance sterility maintenance of the various components, such as the fluid transfer device, located within shield wall 56. Sealing ribs 60 can be configured from various viscoelastic materials, such as rubber products, silicone products, or the like, to enhance the sterility-maintaining characteristics of cap 50. If sealing ribs 60 are formed from the same material forming cap 50, it will appreciated that various elastic materials can be applied to sidewall 33 to cooperate with the sealing ribs to enhance sealing performance between the sealing ribs and the sidewall of the collar.

A ring 61 is provided adjacent proximal end 52 of protective cap 50. Ring 61 includes an annulus section 62 having an interior surface 68. Interior surface 68 defines a proximally respective of the collar. Ring 61, together with protective cap 50, is urged proximally along sidewall 33 of the collar, with interior surface 68 of annulus 62 thrust into covering relationship with engaging surface 38 of the deflectable latches 36. Locking rib 70 is positioned into notch 40 located at the proximal edge of engaging surface 38. The dimensions of the cap and collar can be configured such that when locking rib 70 is engaged with notch 40, proximal end 34 of the collar rests against an inner shoulder 120 of the cap, preventing further proximal movement of the cap vis-a-vis the collar. Owing to the smaller diameter "Y" of annulus 62 vis-a-vis diameter "X" presented by diametrically opposed engaging surfaces 38, annulus 62 exerts an inwardly directed force upon the latches. The effect is to lockingly secure the latches to the vial rim via the secure engagement between underside portion 24*b* of the vial rim and engagement surface 37 of the deflectable latches. The various components can be configured such that when collar 30 and protective cap 50 are locked to the vial rim, the various sealing elements such as stopper 102 and secondary seal 104 (not shown) remain disposed in the vial neck in a ready-to activate state. Accordingly, vial 10 remains in a sterile, ready-to-use state.

Figure 10:
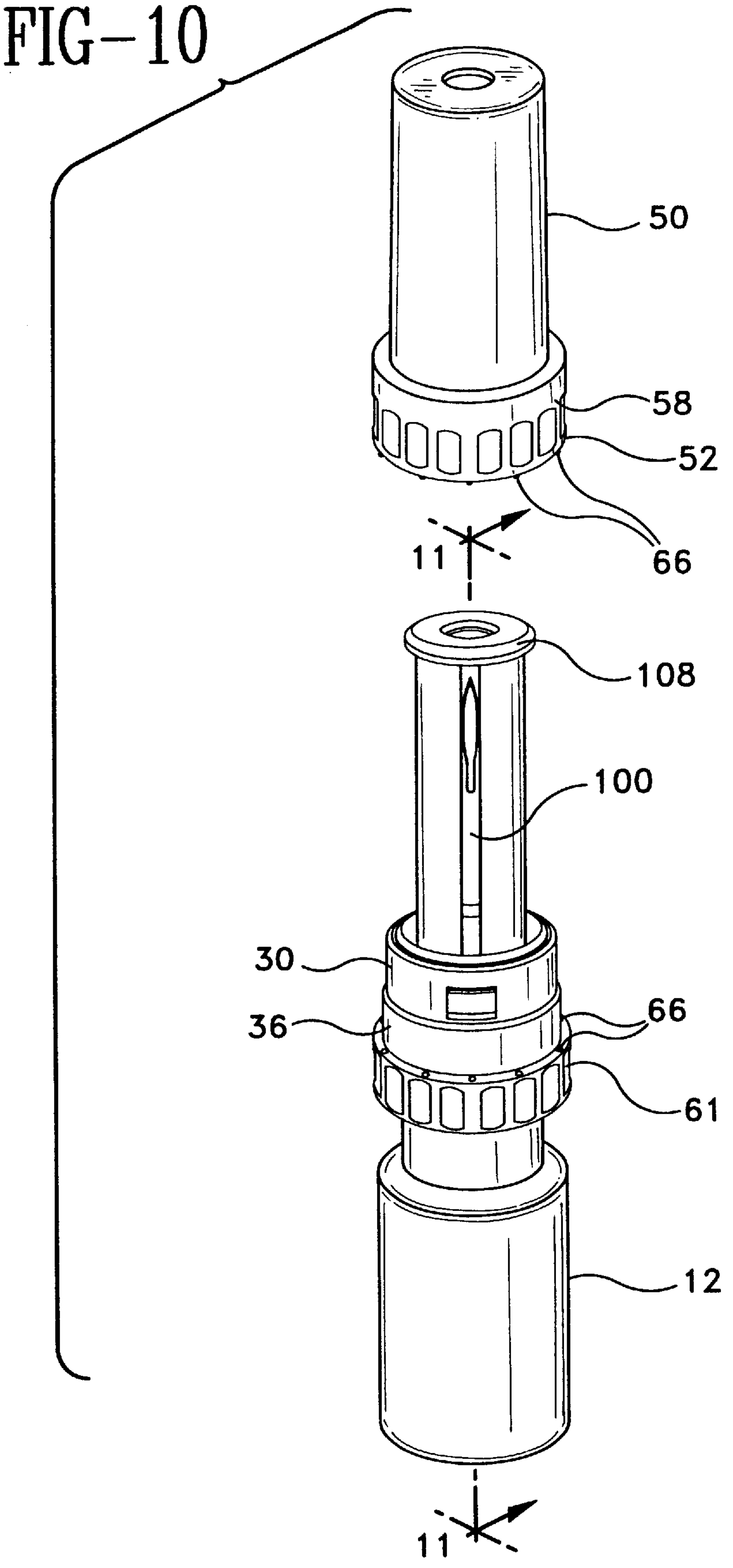
FIG. 10 is an exploded view illustrating a user separating the user-severable connections between the cap and the ring in preparation of using the device.

In order to reconstitute dry drug 26 held in vial 12, the end-user must sever the user-severable connections 66 existing between proximal end 52 of the protective cap and ring 61. As illustrated in FIG. 10, a user, by applying digital pressure to ring 61, may either twist or axially pull cap 50 away from the ring in order to sever connections 66. Protective cap 50 is simply lifted away from ring 61, exposing the fluid transfer device and associated components. Ring 61, by virtue of locking rib 70, remains in secure engagement with latches 36. It will be appreciated by the skilled artisan that any disruptions or breaks in user-severable connections 66 can be employed as tamper-evident means for the user, assuring integrity of drug 26 held therein.

Figure 11:
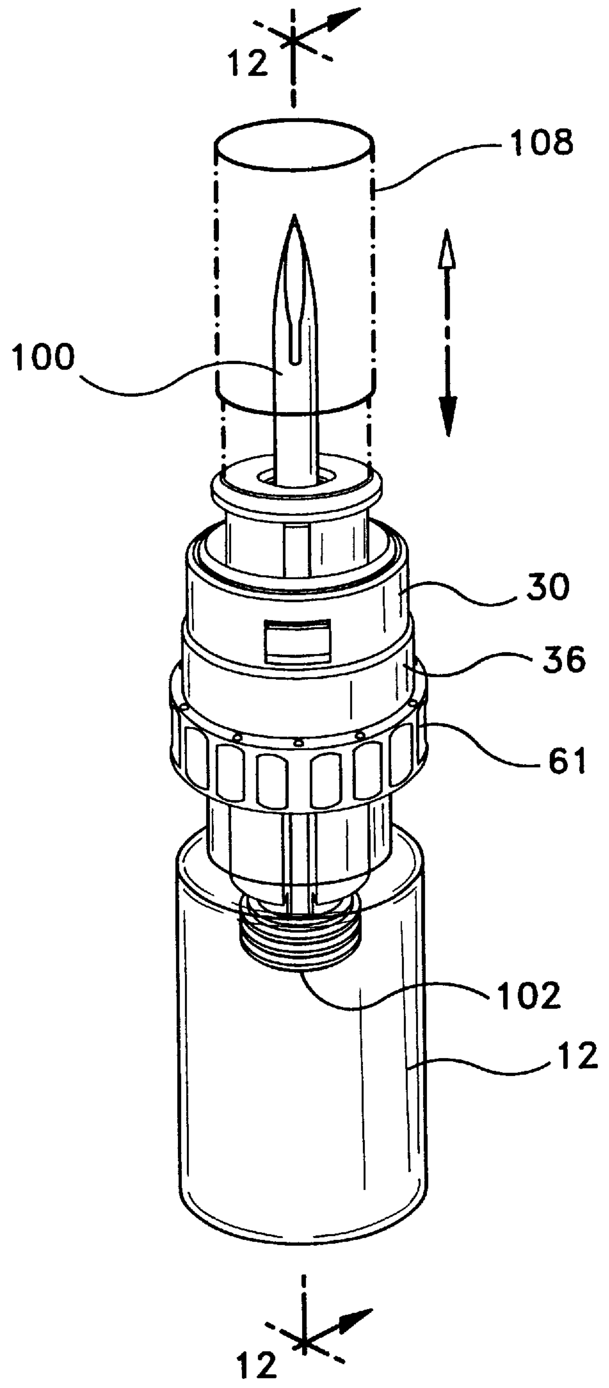
FIG. 11 illustrates, in perspective view, activation of the fluid transfer device associated with the vial connector in preparation of a reconstituting a dry drug held within the vial.
Figure 12:
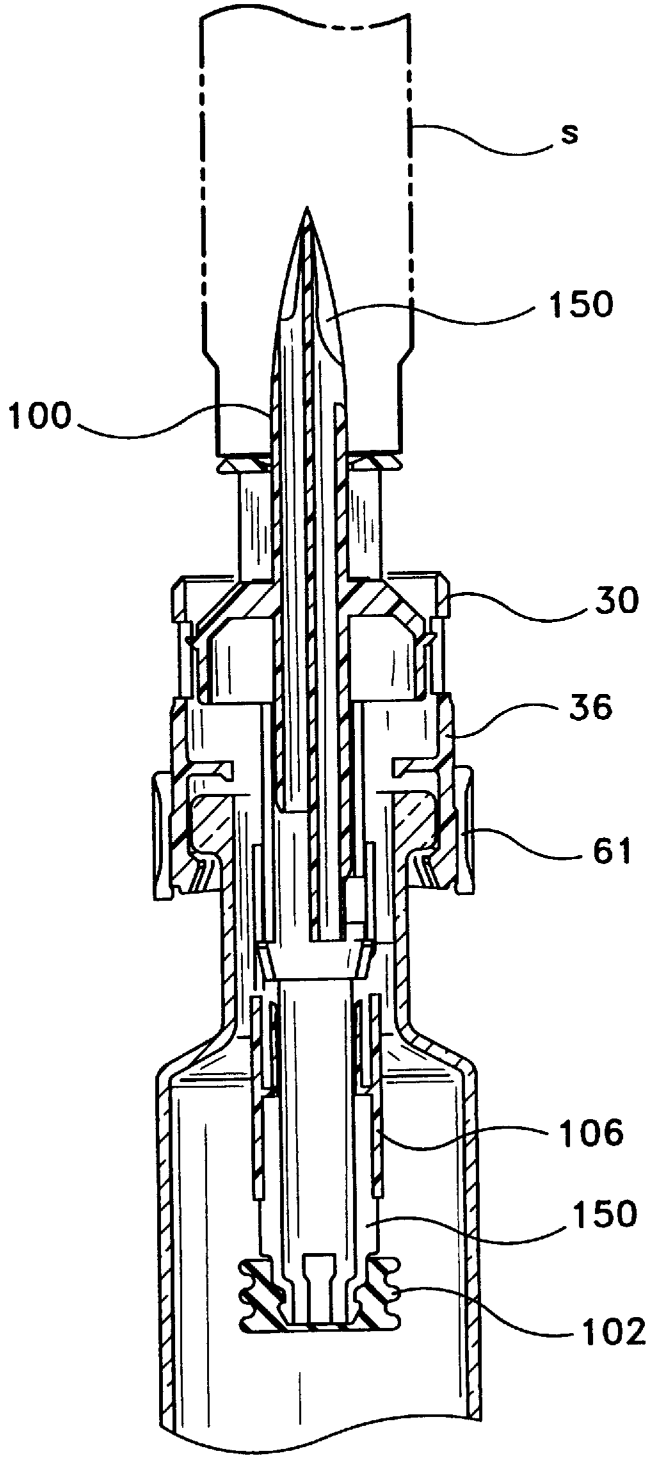
FIG. 12 illustrates, in cross-section, a reconstitution operation.

FIGS. 11 and 12 illustrate activation of fluid transfer device 100 and associated components in preparation of reconstituting drug 26 held within vial 12. For example, protective shield 108 can be thrust proximally, causing proximal motion of secondary seal 104 and stopper 102 towards the interior of vial 12. The effect is to open fluid path 150 between fluid transfer device 100 and the interior of vial 12, enabling fluid passage to and from a source of solvent "S". The skilled artisan will appreciate the mechanisms by which such fluid transfer devices can be employed with the vial connector of the present assembly, for instance, by making reference to U.S. Pat. No. 5,358,501, whose disclosure is incorporated by reference herein. diameter "Y" at least equal to, if not slightly less than, diameter "X" defined between a diametrically opposed pair of engagement surfaces 38. Ring 61 is affixed to proximal end 52 of the cap by one or more user-severable connections 66. As principally disclosed herein, user-severable connections 66 can be formed as one or more frangible connections between the ring and the protective cap. The frangible connections can be formed as thinned sections of material linking the ring and the cap. However, it will be evident to the skilled artisan that other user-severable connections, such as threaded connections, can also be employed. A locking rib 70 is formed adjacent an open proximal end 64 associated with ring 61. A groove 71 disposed on interior surface 68 intermediate severable connections 66 and proximal end 64 can also be provided.

Operation of the connector assembly 10 in conjunction with its various stages shall now be described, making reference to FIGS. 5–14.

Figure 5:
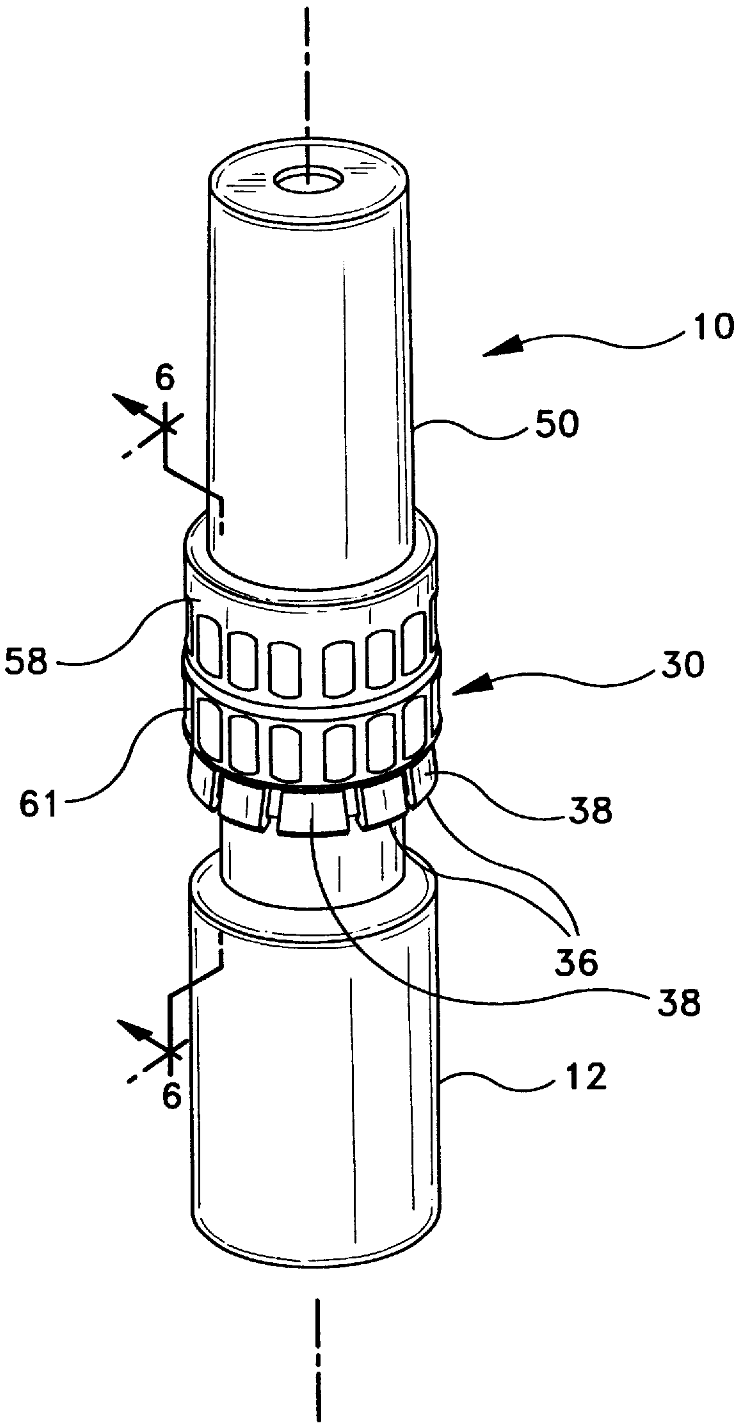
FIG. 5 is a perspective view illustrating the cap engaged with collar, for instance, when the vial and connector assembly are shipped to a pharmaceutical manufacturer for processing.
Figure 6:
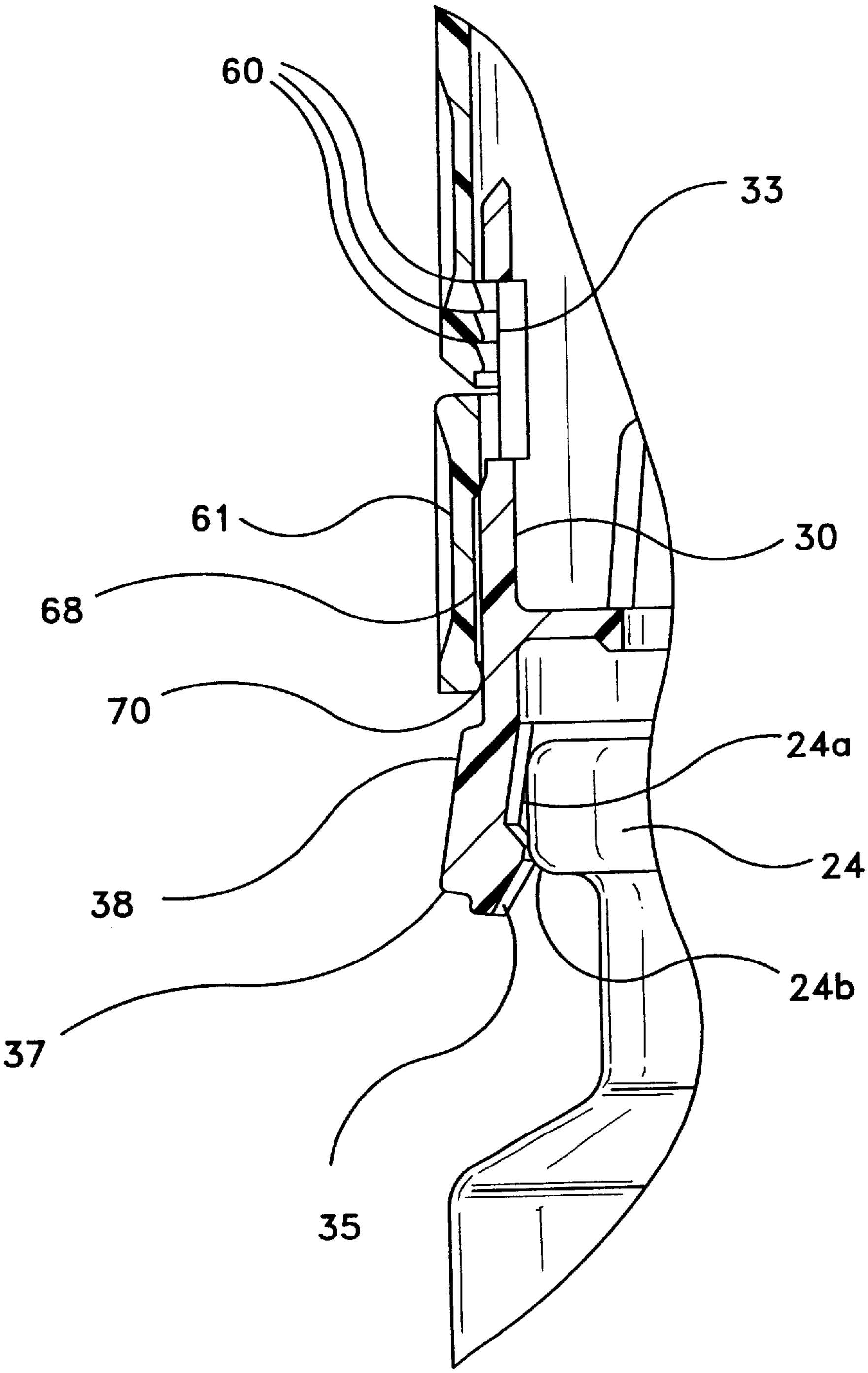
FIG. 6 is a partial cross-sectional view of the cap engaged with the collar taken along line 6—6 of FIG. 5.

FIGS. 5 and 6 are illustrative of vial connector assembly 10 as it might be shipped to a pharmaceutical manufacturer for processing and filling with a given drug 26. For instance, the device may be shipped such that collar 30 is disposed with respect to vial rim 24 in a removable manner. Locking surface 37 rests somewhat adjacent side portion 24*a* of the vial rim, without being placed into secure engagement with underside portion 24*b* of the vial rim. The various sealing components 102, 104 associated with fluid transfer device 100 can be engaged within vial neck 20 (not shown). Cap 50 is placed over collar 30 in a manner such that interior surface 68 of annulus 61 rests over a portion of side wall 33 located distally of engaging surface 38. It will be seen that deflectable latches 36 are canted in an outward manner away from central axis "Z" of collar 30. Sealing ribs 60 of the protective cap are disposed for engagement with sidewall 33 of the collar as previously described. The pharmaceutical manufacturer can remove the cap and collar distally away from the vial rim in order to process and otherwise fill a drug in vial 12.

Figure 7:
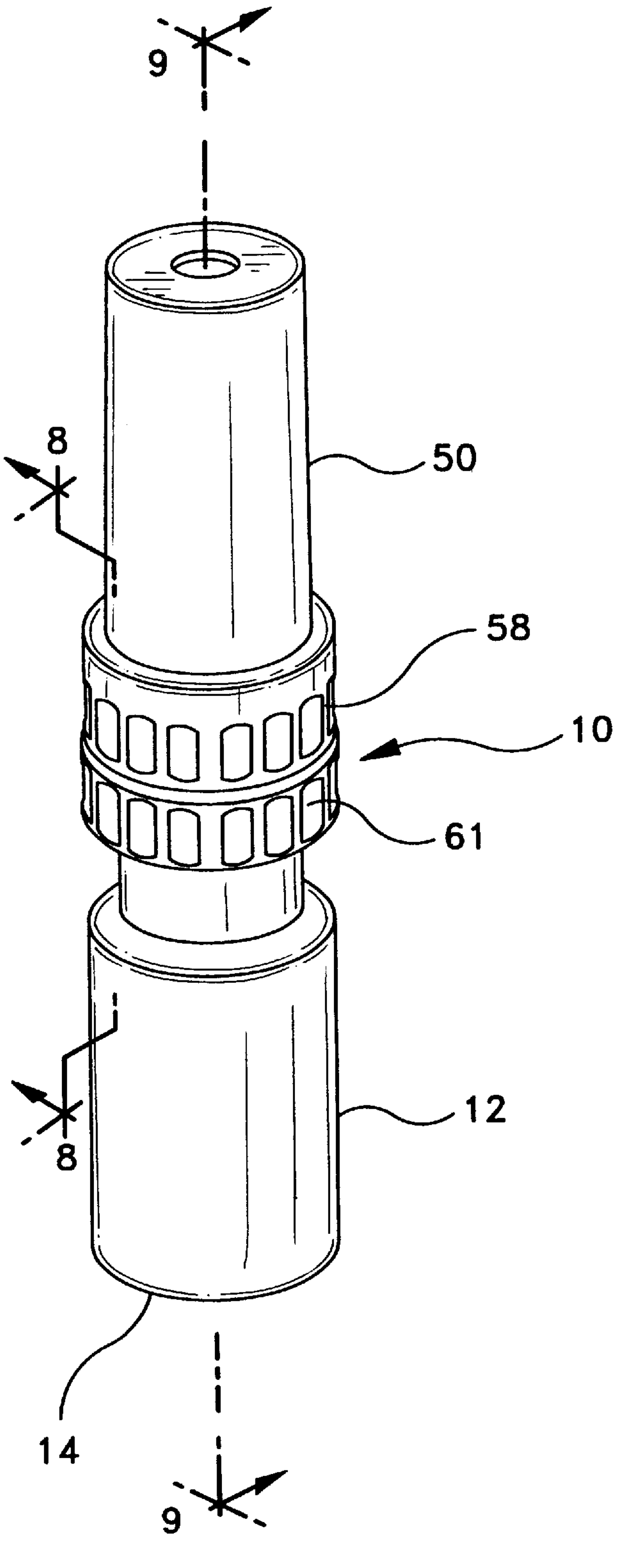
FIG. 7 is a perspective view illustrating the cap engaged with the collar, for instance, after a drug has been processed by a pharmaceutical manufacturer.
Figure 8:
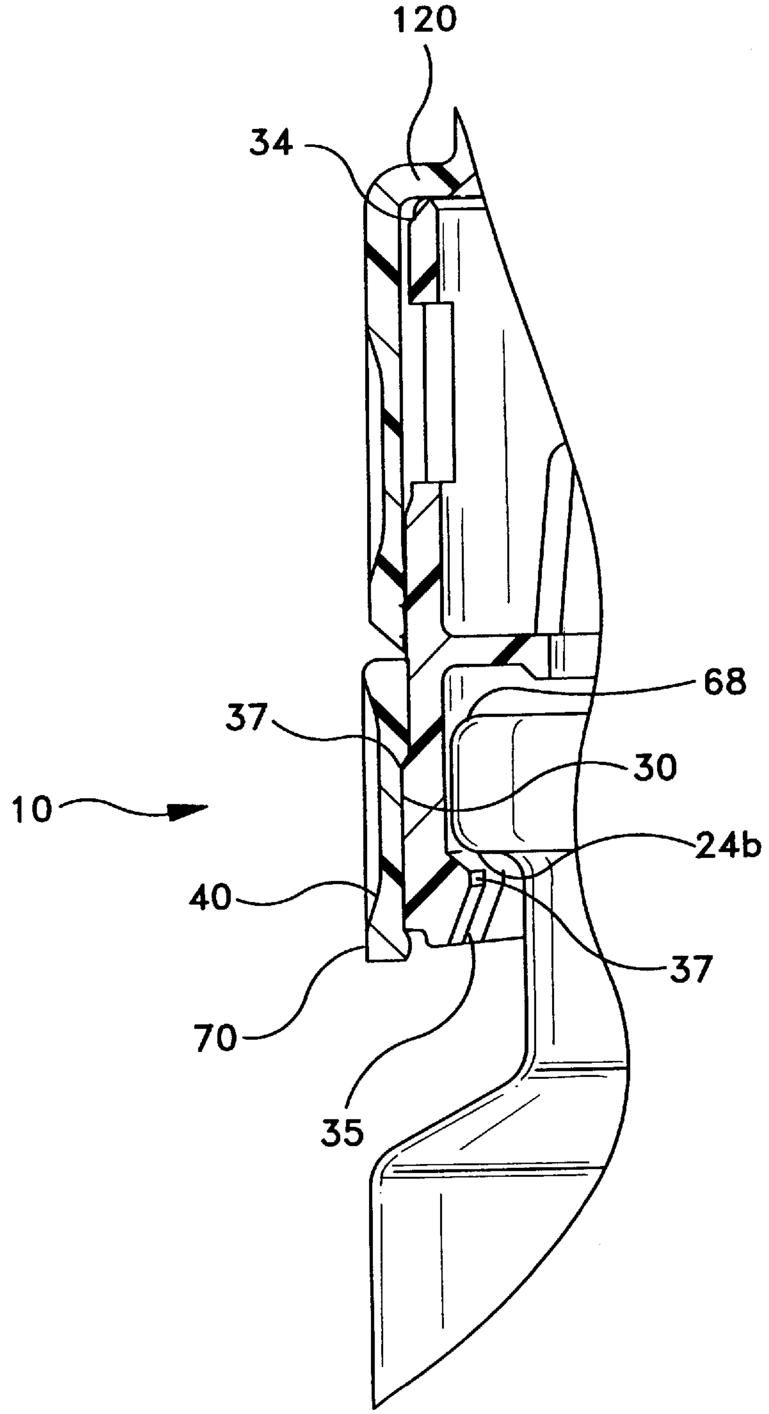
FIG. 8 is a partial cross-sectional view of the cap engaged with the collar taken along line 8—8 of FIG. 7.
Figure 9:
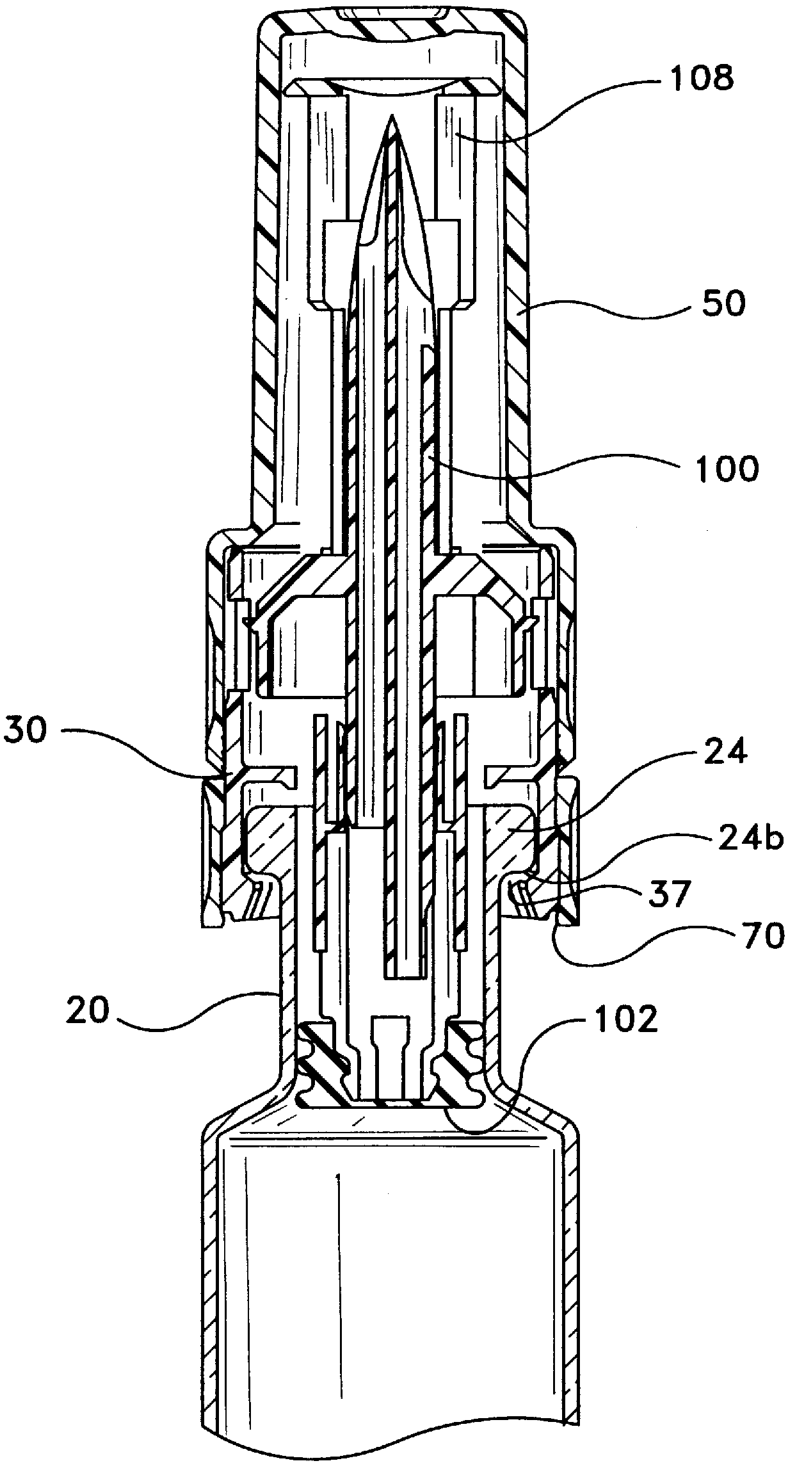
FIG. 9 is a cross-sectional view of the cap engaged with the collar as taken along line 9—9 of FIG. 7.
Figure 13:
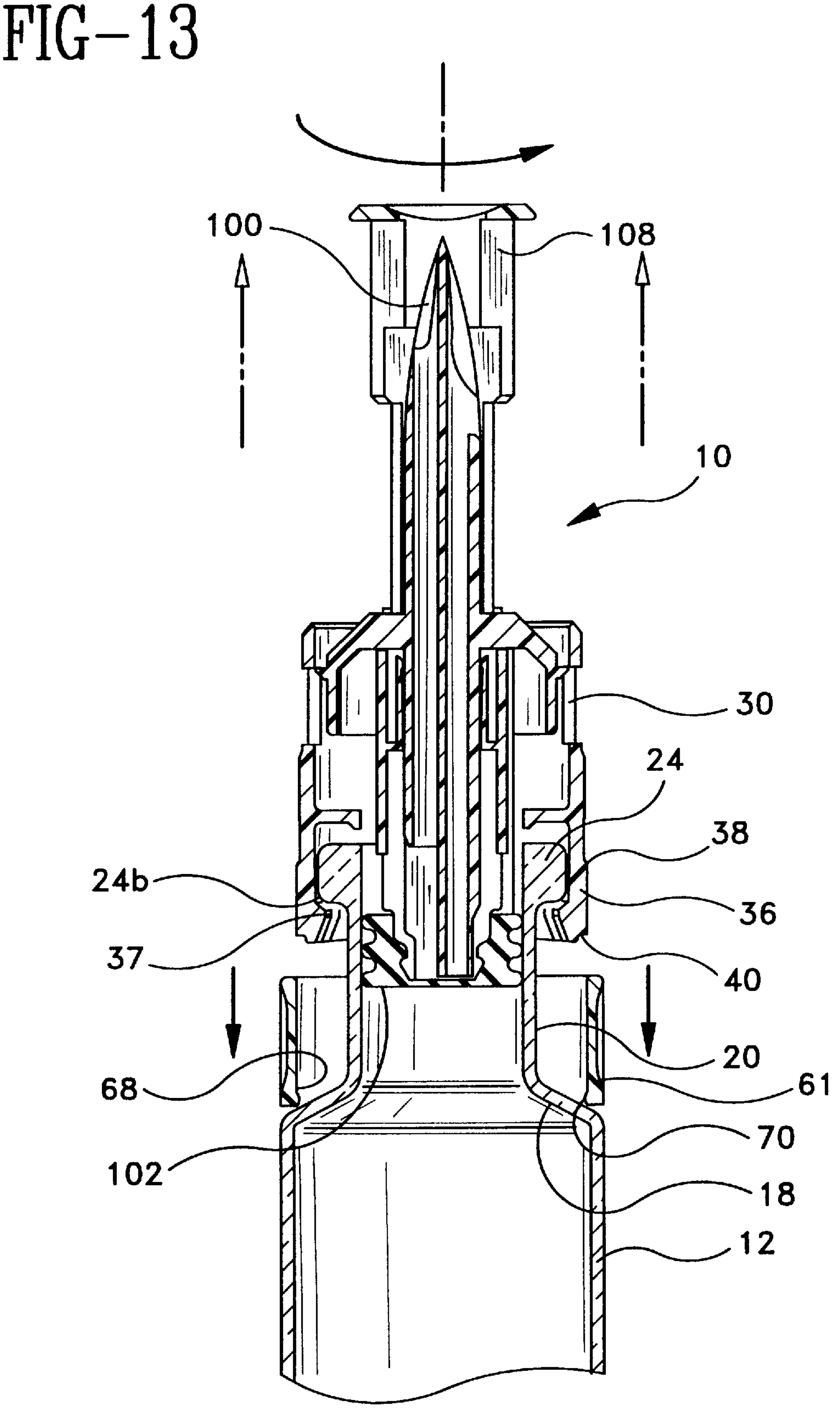
FIG. 13 illustrates, in cross-section, moving the annulus ring in a proximal direction away from engagement with the collar in preparation of removing the vial connector from the vial.
Figure 14:
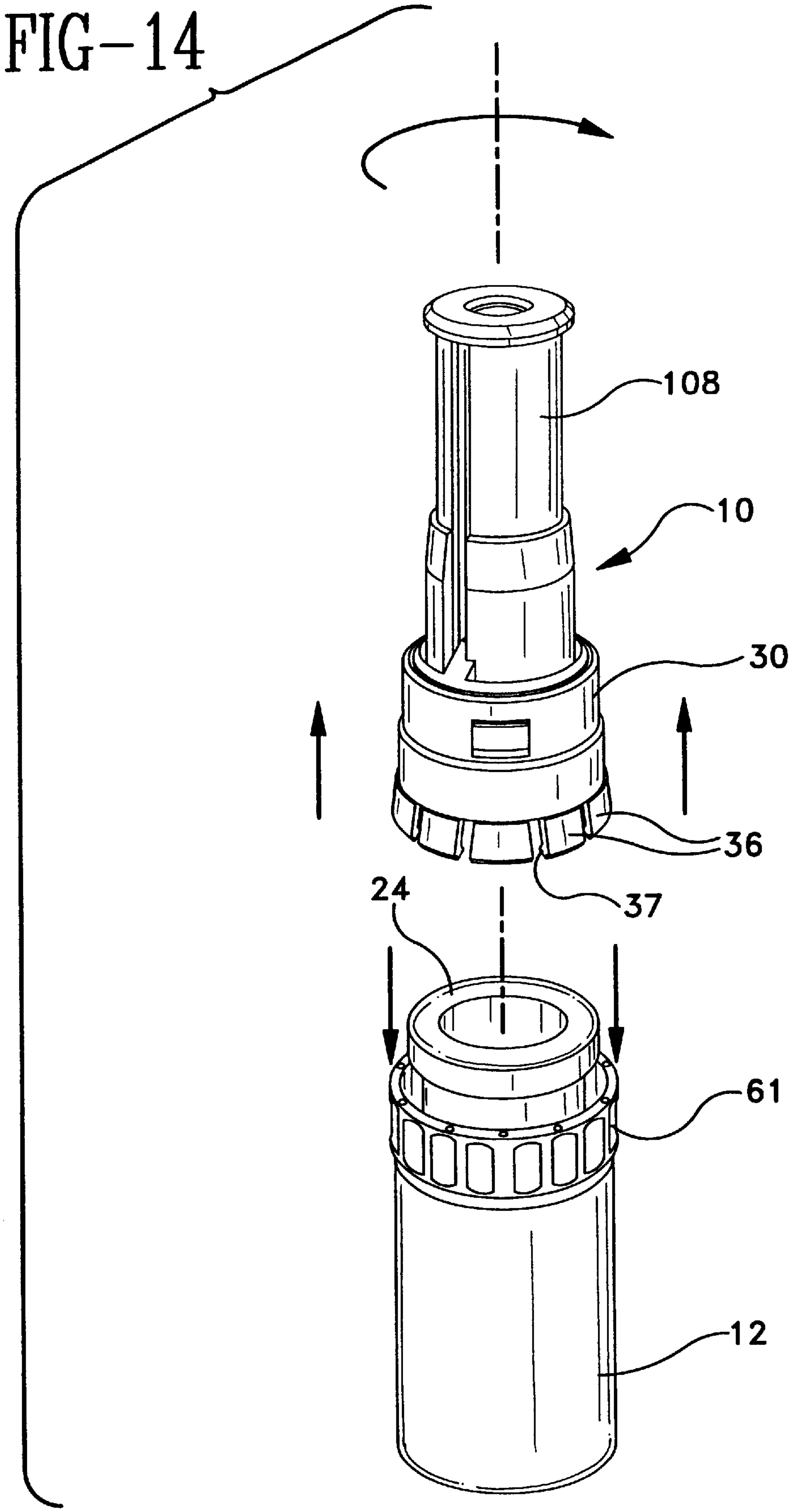
FIG. 14 is an exploded view illustrating removing the vial connector from the vial.

After drug 26 has been filled and otherwise processed within the vial, the pharmaceutical manufacturer can secure vial connector 10 to the vial rim, as seen in FIGS. 7–9. Collar 30 and cap 50 are first returned to the positions illustrated in FIGS. 5 and 6. Thereafter, either by applying a proximally directed force onto protective cap 50, or by applying a distally-directed force onto vial 12, collar 30 and protective cap 50 are urged proximally respective of rim 24. Aided by canted surfaces 35, collar 10 is urged proximally of vial rim 24*b* such that locking surfaces 37 are urged against underside portion 24*b* of the vial rim. Collar 30 is thus placed in locked position respective of rim 24, and further proximal movement of the collar is arrested. Cap 50 continues to move Assuming now that drug 26 held within the vial has been reconstituted and a desired quantity delivered to a patient, a user will be desirous of disposing of the device, particularly vial 12 and vial connector assembly 10, in a safe and judicious manner. If desired, the end-user may disconnect vial connector assembly 10 from vial 12, enabling both to be disposed of separately. Referring to FIGS. 13 and 14, in preparation of safe disposal, a user may wish to re-engage any safety implements provided, such as safety shield 108, so as to protect the user from inadvertent touch contact with fluid transfer device 100. For example, in the device disclosed by U.S. Pat. No. 5,358,501, a needle guard is inherently part of the design. Securely gripping a portion of collar 30 with one hand, a user urges a proximally directed force onto ring 61. Ring 61 is caused to slide proximally away from latches 36, such that the ring will remain freely disposed about neck 20 of the vial. In the absence of an inwardly directed force between interior surface 68 of the annulus and engagement surface 38 of the latches, a user may simply exert a proximally-directed force upon collar 30 to remove same from vial neck 24. Deflectable latches 36, assisted by the inward canting of locking surfaces 37, will slide from engagement with underside portion 24b of the vial rim and around side portion 24*a* of the vial rim, permitting removal of collar 30. Vial connector assembly 10, inclusive of fluid transfer device 100 and the sealing components such as rubber stopper 102, are removed from vial 12. Fluid transfer device 100 is safely sheathed by any safety apparatus such as shield 108. Vial 12 may now be separately disposed of from vial connector 10 in any manner conforming to governmental regulations or industry practice standards.

The various components can be constructed from materials standard in the art. For example, collar 30, cap 50, ring 61 or any of their sub-components can be injection molded from conventional thermoplastics. Fluid access device 10 can be formed from thermoplastics (e.g., if the fluid access device is formed as a spike or luer connector, for instance), or it can be provided as a cannula made from stainless steel (if the cannula is sharp) or from a suitable thermoplastic (for instance, if the cannula is blunt). Various rubbers or elastomeric materials can be chosen for stoppers 102, 104. The vial can be formed from suitable glass or plastics materials adaptable to the particular drug held therein.

It will be appreciated and understood by those skilled in the art that further and additional forms of the invention may be devised without departing from the spirit and scope of the appended claims, the invention not being limited to the specific embodiments shown.

What is claimed is:

1. A connector assembly mountable to the neck of a vial, the neck provided with a rim at an open proximal end of the vial, the rim having a side portion and an underside facing away from the open proximal end of the vial, comprising:

a collar mountable to the rim of the vial neck between a first position, wherein the collar is removably secured to the rim of the vial neck, and a second position, wherein the collar is fixedly secured to the rim of the vial neck, said collar including a proximal end, a distal end, and a sidewall therebetween, a plurality of deflectable latches provided adjacent the proximal end of the collar, each of said latches including locking means deflectable about the side portion of the rim for secured engagement with the underside of the rim when the collar is in said second position;

a protective cap mountable about the sidewall portion of the collar, the protective cap having an open proximal end, a closed distal end, and a shield wall formed therebetween, a ring provided adjacent the open proximal end of the cap and connected thereto by a user-severable connection, said ring having an annulus section with an interior surface cooperable with the locking means of the latches to secure said collar in said second position, the cap having a removable position, wherein the collar is in said first position and said cap is mountable to the collar such that the annulus section is located distally of said locking means, and an engagement position, wherein the cap is urged in a proximal direction such that the interior surface of said annulus section is positioned in cooperating relation with the locking means of said latches to secure the collar in said second position.

2. The connector assembly of claim 1, wherein said protective cap is removable from said engagement position by releasing the user-severable connection between said ring and said protective cap.

3. The connector assembly of claim 1, wherein said severable connection comprises one or more frangible sections located between the proximal end of said protective cap and said ring.

4. The connector assembly of claim 1, wherein said user-severable connection comprises a threaded connection between the proximal end of said protective cap and said ring.

5. The connector assembly of claim 1, wherein said locking means comprises:

a locking element located at a proximal end of the locking means; and an engagement surface secured in functional relation with said locking element and cooperable with the interior surface of said annulus section, wherein when said ring is urged in the proximal direction, the interior surface of said annulus section will be thrust into covering relation with the engagement surface to transmit an inwardly-directed force to said locking element to retain same in secured relation with the underside of said rim.

6. The connector assembly of claim 5, wherein the interior surface of said annulus section includes a rib element adjacent the proximal end of the ring, wherein said rib element is cooperable with said engagement surface when the ring is urged in the proximal direction to prevent removal of said ring in a distal direction.

7. The connector assembly of claim 6, wherein said annulus section is removable from said engagement surface in a proximal direction, wherein in the absence of said inwardly-directed force upon said locking element, said locking elements are deflectable about the side portion of the rim to remove the collar from the vial.

8. A connector assembly mountable to the neck of a vial, the neck provided with a rim at an open proximal end of the vial, the rim having a side portion and an underside facing away from the open proximal end of the vial, comprising:

a collar mountable to the rim of the vial neck between a first position, wherein the collar is removably secured to the rim of the vial neck, and a second position, wherein the collar is fixedly secured to the rim of the vial neck, said collar including a proximal end, a distal end, and a sidewall therebetween, a plurality of deflectable latches provided adjacent the proximal end of the collar, each of said latches including locking means comprising a locking hook deflectable about the side portion of the rim for secured engagement with the underside of the rim when the collar is in said second position and an engagement surface disposed in functional relation with said locking hook, wherein a pair of opposed engagement surfaces defines a first diameter;

a protective cap mountable about the sidewall portion of the collar, the protective cap having an open proximal end, a closed distal end, and a shield wall formed therebetween, a ring provided adjacent the open proximal end of the cap and connected thereto by one or more user-severable connections, said ring having an annulus section defining an interior surface with a second diameter equal to or less than the first diameter of the pair of opposed engagement surfaces, said interior surface cooperable with the locking means of the latches to secure said collar in said second position, the cap having a removable position, wherein the collar is in said first position and said cap is mountable to the collar such that the annulus section is located distally of said locking means, and an engagement position, wherein the cap is urged in a proximal direction such that the interior surface of said annulus section is positioned in cooperating relation with the engagement surface of locking means of said latches to exert a force onto the locking hooks, urging said locking hooks into secured engagement with the underside of the rim to secure the collar in said second position.

9. The connector assembly of claim 8, wherein the sidewall of the collar defines a first plane and wherein the engagement surface of said locking means defines a second plane not co-planar with the first plane of the sidewall.

10. The connector assembly of claim 9, wherein said deflectable latches are canted from the first plane of said sidewall.

11. The connector assembly of claim 8, wherein said annulus section defines a first diameter and a pair of opposed latches define a second diameter, wherein the first diameter is equal to or less than the second diameter.

12. The connector assembly of claim 8, wherein the interior surface of said annulus section includes a rib element adjacent the proximal end of the ring, wherein said rib element is cooperable with said engagement surface when the ring is urged in the proximal direction to prevent removal of said ring in a distal direction.

13. The connector assembly of claim 12, wherein said annulus section is removable from said engagement surface in a proximal direction, wherein in the absence of said inwardly-directed force upon said engagement surface, said locking hooks are deflectable about the side portion of the rim to remove the collar from the vial.

14. The connector assembly of claim 8, wherein said collar is formed of a thermoplastic material.

15. The connector assembly of claim 8, wherein said protective cap is formed of a thermoplastic material.

* * * * *